Figure 1:
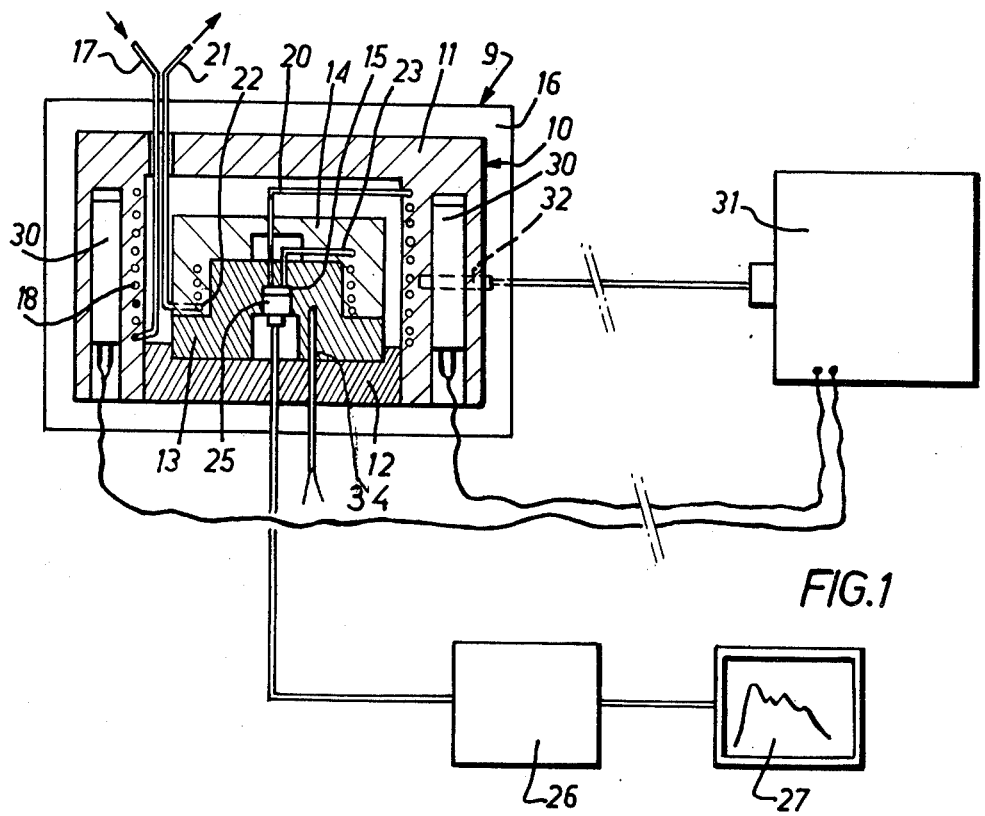

United States Patent [19]

Peyrouset et al.

[11] 3,962,907

[45] June 15, 1976

[54] VISCOMETER

[75] Inventors: André Peyrouset, Ger; Roland Prechner, Jurancon, both of France

[73] Assignee: Ato Chimie, Courbevoie, France

[22] Filed: Apr. 9, 1975

[21] Appl. No.: 566,435

[30] Foreign Application Priority Data
Apr. 17, 1974    France .................................. 74.13281

[52] U.S. Cl. .............................................. 73/55
[51] Int. Cl.² ...................................... G01N 11/08
[58] Field of Search ............................ 73/55, 61.1 C

[56] References Cited
UNITED STATES PATENTS
| | | | |
|---|---|---|---|
| 2,322,814 | 6/1943 | Binckley ................................ | 73/55 |
| 3,548,638 | 12/1970 | Uchida et al. ......................... | 73/55 |

*Primary Examiner*—Donald O. Woodiel
*Assistant Examiner*—Joseph W. Roskos
*Attorney, Agent, or Firm*—Burgess, Ryan and Wayne

[57]    ABSTRACT

A viscometer comprises a liquid feeding conduit opening into a measuring chamber and a capillary liquid outlet conduit connected to said chamber, pressure-sensitive means associated with said chamber for sensing the pressure variations in the latter, converting means for converting the pressure variations sensed by said pressure sensitive means into measurable and displayable quantities of value, said feeding and capillary conduits and said pressure-sensitive means being enclosed in a metallic block arranged in a heat-insulated space which includes heating means for heating said block, said heating means being adapted to maintain the temperature of said block at an adjustable predetermined value.

6 Claims, 2 Drawing Figures

U.S. Patent   June 15, 1976   3,962,907

VISCOMETER

The instant invention is related to a viscometer, and more particularly to a viscometer adapted to be associated with an installation for gel permeation chromatography (G.P.C.). It is known that this chromatographic technique is currently used on a large scale for characterizing the distribution curves and the masses of synthetic or natural polymers. The separation of the molecules within the chromatographic column is effected as a function of their hydrodynamic volume which is proportional to the product $(\eta)M$, wherein $(\eta)$ is the intrinsic viscosity, and M the molecular mass. With a view to being able correctly to appreciate the mass M it is thus necessary for the user to be able to measure at every moment the viscosity of the solution at the outlet of the column, which is rendered possible by the viscometer according to the present invention.

It will be well understood that this application is not the single possible application of the instant viscometer; indeed, the viscometer according to the instant invention may also be used for characterizing the ramification ratio of the macro-molecules and, in a more general manner, for characterizing all the structural parameters of the considered molecules.

The fact that the viscosity is known at every moment may also be used for controlling or monitoring the production of a production unit by means of the measurement of the viscosity, in a manner similar to the monitoring of such production by means of the measurement of a different physical characteristic value, for instance by means of the measurement of the index increment dn/dc by a refractometric method.

An automatic dilution viscometer is already known. This viscometer is based on the well known principle according to which the duration of the flow of a solution through a capillary tube is measured. Certain users have adapted this viscometer to the outlet of a liquid phase chromatograhic column, however, this device allows the viscosity to be measured only in an intermittent manner. Consequently, this known device does not measure the instantaneous viscosity, but only the viscosity of more or less substantial fractions of the volume of the eluate; this results in a lack of accurateness of the interpretation of the viscosity values thus obtained.

Furthermore, the above-mentioned known device is very bulky, and consequently it is difficult to control the temperature in said device. This is a most important drawback, as the viscosity considerably varies with small temperature variations; indeed, in practice it is necessary to control the temperature with an accurateness on the order of 1/1000°C.

To the best knowledge of the applicant, only one continuously operating viscosimetric detecting device has been described in the prior literature (Journal of Polymer Science — Part A.1., vol. 10, 2169–2180, 1972).

This device is substantially constituted by a capillary tube, a measuring chamber having a volume of several microliters, and a pressure-sensitive device mounted on said chamber; as soon as the solution flows through the capillary tube, the pressure within the chamber increases proportionally to the viscosity of the solution. The temperature in this device is regulated by a heating liquid, the temperature of which is controlled by thermostatic means.

It is an object of this instant invention to provide a viscometer of the type described herein-above which is able to operate in a continuous manner.

More particularly it is an object of the instant invention to provide a viscometer of the type considered which is able to operate at elevated temperatures, e.g. 150°C and more, and which furthermore has a high operational stability.

A viscometer according to the invention comprises a liquid feeding conduit opening into a measuring chamber and a capillary liquid outlet conduit connected to said chamber, pressure sensitive means associated with said chamber for sensing the pressure variations in the latter, converting means for converting the pressure variations sensed by said pressure-sensitive means into measurable and displayable quantities of value, said feeding and capillary conduits and said pressure-sensitive means being enclosed in a metallic block arranged in a heat-insulated space which includes heating means for heating said block, said heating means being adapted to maintain the temperature of said block at an adjustable predetermined value.

Due to the above-defined arrangement a high thermal stability is obtained, especially on account of the particularly uniform heat distribution in said metallic block.

According to another feature of the instant invention the feeding conduit and the capillary conduit are each constituted by a coiled tube, said coiled tubes being arranged coaxially with respect to the measuring chamber, one end of each one of said conduits being connected to said measuring chamber while the other end of each one of said conduits issues from said heat insulated space.

This arrangement considerably improves the heat distribution, and the latter is still more markedly improved by the fact that the heating means comprise electrically heated rods which are fed from a temperature control installation comprising a regulating probe incorporated in said block and a thermo-couple for measuring the temperature.

These and other features — especially features related to the use of the present invention for measuring the viscosity of the liquid issuing from a gel permeation chromatography column — will become apparent from the following description which refers to the appended drawings, and which is given by way of example only, but not by way of limitation.

FIG. 1 is a schematic view, partially in section, of one embodiment of the viscometer in accordance with the present invention.

Figure 2:
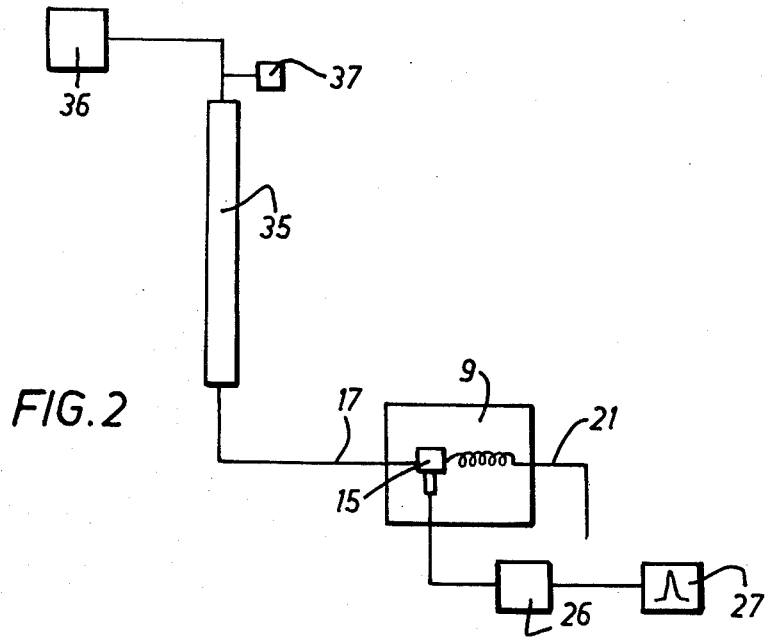

FIG. 2 schematically shows an installation for measuring the viscosity of the liquid issuing from a gel permeation chromatography column.

In the embodiment shown in FIG. 1 the viscometer according to the invention comprises a metallic core 10 constituted — for reasons related to manufacturing problems — by a plurality of interfitted metallic elements, such as the external element 11 fitted on a base 12 on which is arranged an element 13 on which, in turn, is fitted an element 14. It will be noted that the configuration of these elements 11 through 14 and the empty spaces which may be defined between said elements so as to facilitate for example the assembly operations, are by no means critical. In accordance with the instant invention it is important only to provide a core or block 10 having a comparatively compact shape.

This core or block 10 is surrounded by a heat-insulated space 16 and a case 9; said block or core 10 has arranged therein a measuring chamber 15 having a very small volume, preferably lower than 10 micro-liters, to which are connected a feeding conduit and a capillary conduit adapted, respectively, to feed a liquid into said chamber and to evacuate said liquid therefrom.

The feeding conduit comprises a straight portion 17 passing through the heat-insulated space, as well as a coil 18 connected to said straight portion and embedded in element 11 so as to be coaxial to chamber 15, and connected to the latter by a conduit 20.

In a similar manner the capillary outlet conduit comprises a straight portion 21 passing through space 16 and a coil 22 embedded in element 14 so as to be coaxial to chamber 15, and connected to the latter by a conduit 23.

A pressure detector 25 is mounted in chamber 15 and is adapted to detect the pressure variations within said chamber. This pressure detector may comprise for instance a resistance the length of which varies as a function of said pressure, said resistance being connected in a Wheatstone bridge. Any convenient known means may be used for exploiting the unbalance which is thus produced in said bridge. This unbalance may e.g. be amplified by an amplifier 26, and the amplified signal issuing therefrom may be displayed or recorded by convenient means at 27.

The viscometer according to the invention further comprises heating means which in the embodiment shown are constituted by heating rods 30 which are also embedded in block 10 and supplied from a temperature control installation 31 including a temperature probe 32 incorporated in said block.

A thermo-couple 34 allows the temperature of the block, and consequently the temperature of chamber 15 and the temperature of the liquid it contains, to be measured. Indeed, on account of the length of the trajectory as determined by the coils, this liquid is in a state of temperature equilibrium with respect to the block.

FIG. 2 illustrates schematically the arrangement of the viscometer according to the invention, associated with a gel permeation chromatography column 35 which comprises a pump 36 and an injector 37.

The outlet of the column is connected to conduit 17 and consequently to the measuring chamber 15. The volume of this measuring chamber is reduced, so as to avoid the mixture of fractions having different molecular masses. The variations of the viscosity of the liquid flowing through said chamber result in variations of the pressure in said chamber which are sensed and displayed or recorded at 27.

The viscometer according to the present invention is adapted to be operated at a high temperature, e.g. 150°C and higher, and to be operated in a substantially continuous manner.

It will be well understood that the invention is by no means limited to the embodiment described hereinabove and shown in the appended drawings, and that any person skilled in the art may modify said embodiment in many respects without leaving the scope of the invention as defined in the appended claims.

What is claimed is:

1. A viscometer comprising a metallic block defining a measuring chamber therein, pressure sensitive means in said chamber for sensing pressure variations in said chamber, conversion means for converting pressure variations sensed by said pressure sensitive means into displayable signals, heating means coupled to said block for heating said block to an adjustable predetermined temperature, liquid inlet conduit means connected to said chamber including a first coil within said block and surrounding said chamber, capillary liquid outlet conduit means connected to said chamber and including a second coil within said block and surrounding said chamber, temperature measuring means within said block for measuring the temperature of said block, whereby said temperature measuring means also measures the temperature of liquid in said chamber, and heat insulating means surrounding said block.

2. The viscometer of claim 1 wherein said first and second coils are arranged coaxially with respect to said measuring chamber, one end of each of said coils being connected to said measuring chamber, and the other end of each of said first and second coils being connected to respective inlet and outlet conduit portions projecting outwardly of said heat insulating means.

3. The viscometer of claim 1 wherein said heating means comprises electrical heating rods thermally coupled to said block, a temperature probe in said block, and temperature regulating means responsive to said probe for applying heating current to said heating rods.

4. A viscometer comprising a metallic block defining a measuring chamber therein, pressure sensitive means in said chamber for sensing pressure variations in said chamber, said pressure sensitive means comprising resistor means arranged to have a length which varies proportionally with variations of pressure in said chamber, a Wheatstone bridge incorporating said resistor means as an arm thereof, heating means similarly coupled to said block for heating said block to an adjustable predetermined temperature, liquid inlet conduit means connected to said chamber and including a first coil arranged within said block and surrounding said chamber, capillary liquid outlet conduit means connected to said chamber and including a second coil arranged within said block and surrounding said chamber, temperature measuring means in said block for measuring the temperature of said block, whereby said temperature measuring means also measures the temperature of liquid in said chamber, heat insulating means surrounding said block, and recording means for recording output signals of said Wheatstone bridge.

5. The viscometer system of claim 4 for instantaneously and continuously measuring the viscosity of a solution issuing from a liquid phase chromatographic column, comprising means connecting said column to said liquid feeding conduit, whereby said solution flows through said measuring chamber, and whereby variations of the viscosity of said solution produce variations of the pressure in said chamber and variations in the display of said recording means.

6. The viscometer system of claim 4 further comprising amplifier means for amplifying signals applied to said recording means.

* * * * *